US007732401B2

(12) United States Patent
Kojima et al.

(10) Patent No.: US 7,732,401 B2
(45) Date of Patent: Jun. 8, 2010

(54) INHIBITOR OF TGF-β ACTIVATION REACTION

(75) Inventors: Souichi Kojima, Ibaraki (JP); Ryutaro Teraoka, Saitama (JP)

(73) Assignee: Riken, Saitama (JP)

( * ) Notice: Subject to any disclaimer, the term of this patent is extended or adjusted under 35 U.S.C. 154(b) by 117 days.

(21) Appl. No.: 12/044,463

(22) Filed: Mar. 7, 2008

(65) Prior Publication Data

US 2008/0280827 A1     Nov. 13, 2008

(30) Foreign Application Priority Data

Mar. 8, 2007    (JP)    .............................. 2007-058222

(51) Int. Cl.
    *A61K 38/00*    (2006.01)
(52) U.S. Cl. .......................................................... 514/2
(58) Field of Classification Search ...................... None
    See application file for complete search history.

(56) References Cited

U.S. PATENT DOCUMENTS

2008/0038748 A1    2/2008 Kojima et al.

FOREIGN PATENT DOCUMENTS

| JP | 2003-252792 | 9/2003 |
|----|----|----|
| JP | 2004-121001 | 4/2004 |
| JP | 2005-239695 | 9/2005 |
| WO | 2005/023870 | 3/2005 |
| WO | 2005/039570 | 5/2005 |
| WO | WO 2007121233 A1 * | 10/2007 |

OTHER PUBLICATIONS

Swann et al., "Nonspecific Protease-Catalyzed Hydrolysis/Synthesis of a Mixture of Peptides: Product Diversity and Ligand Amplification by a Molecular Trap," Biopolymer, 1998, 40, 617-25.*
Nishiya et al. "A purification method of the diagnostic enzyme Bacillus uricase using magnetic beads and non-specific protease," Protein Expression and Purification, 2002, 25, 426-429.*
Juhasez et al. "The utility of nonspecific proteases in the characterization of glycoproteins by high-resolution time-of-flight mass spectrometry," International Journal of Mass Spectrometry and Ion Processes, 1997, 169/I 70, 217-230.*
Salisbury et al. "Peptide Microarrays for the Determination of Protease Substrate Specificity," JACS, 2002, 124,14868-70.*
Rawlings, N.D., Morton, F.R., Kok, C.Y., Kong, J. & Barrett, A.J. (2008) MEROPS: the peptidase database. Nucleic Acids Res 36, D320-D325.*
Peptide Cutter, http://ca.expasy.org/tools/peptidecutter/peptidecutter_enzymes.html.*
Gomes et al. "Proteolytic Mapping of Human Replication Protein A: Evidence for Multiple Structural Domains and a Conformational Change upon Interaction with Single-Stranded DNA," Biochemistry, 1996, 35, 5586-95.*
Rail et al. "The Domain Structure of Human Receptor-associated Protein, Protease Sensitivity and Guanidine HCI Denaturation," J. Biol. Chem., 1998, 273, 24152-7.*
Speicher et al. "Spectrin Domains: Proteolytic Susceptibility as a Probe of Protein Structure," J. Cell. Biochem., 1982, 18, 479-492.*
Hervivo et al. "Negative selectivity and the evolution of protease cascades: the specificity of plasmin for peptide and protein substrates," Chem. & Bio., 2000, 7, 443-452.*
Lovgren et al. "Enzymatic action of human glandular kallikrein 2 (hK2) Substrate specificity and regulation by Zn2+ and extracellular protease inhibitors," Eur. J. Biochem. 1999, 262, 781-789.*
Sugita et al. "Complete nucleotide sequence of the freshwater unicellular cyanobacterium *Synechococcus elongatus* PCC 6301 chromosome: gene content and organization," Photosynthesis Research, 2007, 93, 55-67, published online Jan. 9, 2007.*
CAS 2007:936363.*
MEROPS http://merops.sanger.ac.uk/, printed Jul. 17, 2009.*
English Language Abstract of JP 2004-121001.
Schuppan et al. "Hepatic Fibrosis—Therapeutic Strategies" *Digestion* 59:385-390 (1998).
Qi et al. "Blockade of type β transforming growth factor signaling prevents liver fibrosis and dysfunction in the rat" *Proc. Natl. Acad. Sci. USA* 96:2345-2349 (1999).
Ueno et al. "A Soluble Transforming Growth Factor β Receptor Expressed in Muscle Prevents Liver Fibrogenesis and Dysfunction in Rats" *Hum. Gene. Ther.* 11:33-42 (2000).
Okuno et al. "Prevention of Rat Hepatic Fibrosis by the Protease Inhibitor, Camostat Mesilate, via Reduced Generation of Active TGF-β" *Gastroenterology* 120(7):1784-1800 (2001).
Akita et al. "Impaired Liver Regeneration in Mice by Lipopolysaccharide Via TNF-α/Kallikrein-Mediated Activation of Latent TGF-β" *Gastroenterology* 123:352-364 (2002).
English Language Abstract of JP 2003-252792.
Schultz-Cherry et al. "Regulation of Transforming Growth Factor-β Activation by Discrete Sequences of Thrombospondin 1" *J. Biol. Chem.* 270(13):7304-7310 (1995).
Crawford et al. "Thrombospondin-1 Is a Major Activator of TGF-β1 In Vivo" *Cell* 93:1159-1170 (1998).
Ribeiro et al. "The Activation Sequence of Thrombospondin-1 Interacts with the Latency-associated Peptide to Regulate Activation of Latent Transforming Growth Factor-β" *J. Biol. Chem.* 274(19):13586-13593 (1999).
Murphy-Ullrich et al. "Activation of latent TGF-β by thrombospondin-1: mechanisms and physiology" *Cytokine & Growth Factor Reviews* 11:59-69 (2000).
Kondo et al. "Molecular Mechanism and Regulation of Latent TGF-β Activation" *Nihon Kessen Shiketu Gakkaishi* (*The Bulletin of the Japanese Society on Thrombosis and Hemostatis*) 14(3):210-219 (2003).

(Continued)

*Primary Examiner*—Cecilia Tsang
*Assistant Examiner*—Christina Bradley
(74) *Attorney, Agent, or Firm*—Greenblum & Bernstein, P.L.C.

(57) ABSTRACT

The present invention aims to provide a substance(s), especially a peptide(s) capable of inhibiting the TGF-β activation reaction. The present invention provides a peptide consisting of 11 to 50 amino acid residues, which comprises an amino acid sequence Gln-Ile-Leu-Ser-X1-X2-X3-X4-Ala-Ser-Pro (SEQ ID NO: 1) wherein each of X1 to X4 independently represents any given amino acid residue, and X1-X2-X3-X4 is a sequence that is not Lys-Leu-Arg-Leu (SEQ ID NO: 12) and is not cleavable by proteases.

7 Claims, 6 Drawing Sheets

OTHER PUBLICATIONS

Annes et al. "Making sense of latent TGFβ activation" *J. Cell Sci.* 116:217-224 (2003).
Greenwell et al. "An enhancement method for immunohistochemical staining of proliferating cell nuclear antigen in archival rodent tissues" *Cancer Letters* 59:251-256 (1991).
English Language Abstract of JP 2005-239695.
Gentry et al. "The Pro Domain of Pre-Pro-Transforming Growth Factor β1 When Independently Expressed Is a Functional Binding Protein for the Mature Growth Factor" *Biochemistry* 29(29):6851-6857 (1990).
U.S. Appl. No. 10/570,606 to Kojima et al.

* cited by examiner

| | |
|---|---|
| QP peptide | QILSKLRLASP |
| QPA peptide | QILSAAAAASP |
| T200 peptide | TGVVRQWLSRG |

PH:partial hepatectomy    ** p < 0.01

QPQ peptide ; QILSQQQQASP

INHIBITOR OF TGF-β ACTIVATION REACTION

TECHNICAL FIELD

The present invention relates to a substance that inhibits the TGF-β activation reaction.

BACKGROUND ART

Transforming growth factor (TGF)-β is a multifunctional, homodimeric cytokine with a molecular weight of 25 kD, and exhibits a variety of biological activities.—e.g. It strongly promotes pathogenesis of sclerotic diseases including hepatic fibrosis/cirrhosis, atherosclerosis, lung fibrosis, scleroderma, renal failure (glomerulonephritis) or myelofibrosis as well as rheumatoid arthritis and proliferative vitreoretinopathy via stimulating the excessive production of extracellular matrices from mesenchymal cells and suppressing the growth of epithelial cells. Furthermore, TGF-β not only suppresses the growth and functions of skin keratinocytes, thereby causing their apoptosis and being deeply involved in epilation, but also suppresses functions of immune cells. It has been shown from the results of studies utilizing neutralizing antibodies against TGF-β in animal models that sclerotic diseases can be prevented or cured by suppressing the activities of TGF-β. For example, it has been reported to block TGF-β's activity at the entrance by employing either antibody therapies with neutralizing antibodies against TGF-β and its receptors, or gene therapies with dominant negative TGF-β receptor genes or soluble TGF-β receptor genes (JP Patent Publication (Kokai) No. 2004-121001 A; Schuppan et al., Digestion 59: 385-390, 1998; Qi et al., Proc Natl Acad Sci USA 96: 2345-2349, 1999; Ueno et al., Hum Gene Ther 11: 33-42, 2000). However since such an antibody therapy and a gene therapy retain problems in having an uncertainty in a necessary amount and an administration method, these methods cannot be immediately applied to the clinics. Thus, a challenge has been underway to develop a low molecular weight inhibitor based on the molecular mechanism of TGF-β's actions.

Using animal models, the present inventors demonstrated that a low molecular weight compound, cytoxazone, inhibits the signal transduction pathway of TGF-β, so as to suppress the pathogenesis of liver diseases (International Publication WO2005/039570). However, a target protein, on which cytoxazone directly acts, has not yet been identified.

On the other hand, by focusing on the fact that TGF-β is generated as an inactive latent molecule and converted to its active form by the action of protease (TGF-β activation reaction), the present inventors demonstrated a possibility that a low molecular weight synthetic protease inhibitor (Okuno et al., Gastroenterology 120: 18784-1800, 2001) as well as an antibody against the proteases (JP Patent Publication (Kokai) No. 2003-252792 A; Akita et al., Gastroenterology 123: 352-364, 2002) can be used to inhibit the TGF-β activation reaction, thereby preventing the diseases in animal models. However, since the current protease inhibitors have a wide range of inhibitory spectrum, there is a severe concern of side effects when applied to humans. Furthermore, since relatively high concentrations will be required for the current antibodies to work, there is a big concern of high costs due to a requirement for purification of a large amount of antibodies when applied to humans.

Moreover, the present inventors identified the cleavage site during the aforementioned TGF-β activation reaction, and succeeded in producing antibodies that recognize the cutting ends, and thus in demonstrating for the first time in the world that the proteolytic TGF-β activation reaction plays an important role in the pathogenesis of human liver diseases using these antibodies (International Publication WO2005/023870).

In the past, a peptide consisting of 8 to 17 amino acids that suppresses the generation of TGF-β in an immortalized hair papilla cell line was reported (JP Patent Publication (Kokai) No. 2005-239695 A). However, underlying action mechanisms thereof, including the possibilities of suppressing gene expression and/or activation reaction, as well as the effectiveness thereof in vivo, has not been shown.

Moreover, the group of Murphy-Ullrich at the University of Alabama, U.S.A. investigated the adherent-type TGF-β activation reaction by a glycoprotein, thrombospondin 1, and reported that TGF-β is activated by binding of KRFK sequence corresponding to amino acid numbers 412-415 of thrombospondin 1 to LSKL sequence corresponding to amino acid numbers 54-57 of LAP, and that the synthetic KRFK peptide activates TGF-β, whereas the synthetic LSKL peptide inhibits the TGF-β activation reaction (Schultz-Cherry et al., J. Biol. Chem. 270: 7304-7310, 1995; Crawford et al., Cell 93: 1159-1170, 1998; Ribeiro et al., J. Biol. Chem. 274: 13586-13593, 1999; Murphy-Ullrich and Poczatek Cytokine & Growth Factor Reviews 11: 59-69, 2000). The LSKL sequence derived from amino acid numbers 54-57 of the aforementioned LAP overlaps with the plasmin cleavage site K56-L57 identified by the present inventors. By binding to and cutting this portion, respectively, thrombospondin 1 and proteases may inhibit a noncovalent bond between this portion and active TGF-β molecule, resulting in release of the active TGF-β molecule from a latent complex (namely the TGF-β activation reaction). The present inventors, however, could not reproduce both the induction of TGF-β activation by the synthetic KRFK peptide and inhibition of TGF-β activation by the synthetic LSKL peptide, in their additional tests. Murphy-Ullrich et al. indicated an involvement of a thrombospondin 1-dependent adherent-type TGF-β activation reaction in the pathogenesis of lung or pancreatic diseases, but not in the pathogenesis of liver diseases.

DISCLOSURE OF THE INVENTION

The present invention aims to solve the aforementioned problems of the prior art techniques. Namely, the present invention aims to provide a substance(s), especially a peptide(s) capable of inhibiting the TGF-β activation reaction.

The present inventors have conducted intensive studies directed towards achieving the aforementioned object. Based on their previous findings that TGF-β expresses its biological activities in the liver only after its activation by proteases such as plasmin and plasma kallikrein, the present inventors have succeeded in synthesizing a peptide(s) capable of stably inhibiting plasmin/plasma kallikrein-dependent TGF-β activation reactions, even when used in a low concentration, thereby completing the present invention.

The present invention provides the followings.

(1) A peptide consisting of 11 to 50 amino acid residues, which comprises an amino acid sequence, Gln-Ile-Leu-Ser-X1-X2-X3-X4-Ala-Ser-Pro (SEQ ID NO: 1), wherein each of X1 to X4 independently represents any given amino acid residue, and X1-X2-X3-X4 is a sequence not cleavable by proteases other than Lys-Leu-Arg-Leu (SEQ ID NO: 12).

(2). The peptide according to (1), wherein X1 and X3 represent amino acid residues other than basic amino acids.

(3) A peptide consisting of 11 to 50 amino acid residues, which comprises the amino acid sequence of any one of the following (i) to (iv):

```
Gln-Ile-Leu-Ser-Ala-Ala-Ala-Ala-Ala-Ser-Pro   (i);
(SEQ ID NO: 2)

Gln-Ile-Leu-Ser-Ala-Leu-Ala-Leu-Ala-Ser-Pro   (ii);
(SEQ ID NO: 3)

Gln-Ile-Leu-Ser-Gln-Gln-Gln-Gln-Ala-Ser-Pro   (iii);
(SEQ ID NO: 4)
and

Gln-Ile-Leu-Ser-Gln-Leu-Gln-Leu-Ala-Ser-Pro   (iv).
(SEQ ID NO: 5)
```

(4) The peptide according to (1), which has a length of 11 to 20 amino acid residues.

(5) A peptide having an amino acid sequence, Gln-Ile-Leu-Ser-X1-X2-X3-X4-Ala-Ser-Pro (SEQ ID NO: 1) wherein each of X1 to X4 independently represents any given amino acid residue, and X1-X2-X3-X4 is a sequence that is not Lys-Leu-Arg-Leu (SEQ ID NO: 12) and is not cleavable by proteases.

(6) An inhibitor comprising the peptide of (1) against the generation of active TGF-β.

(7) A medicament comprising the peptide of (1) for treating and/or preventing any pathologic conditions associated with TGF-β.

(8) A hepatic regeneration promoting agent or hepatic fibrosis suppressing agent, which comprises the peptide of (1).

In a living body, particularly during the pathogenesis of liver diseases, latent TGF-β is cleaved by proteases at a specific portion, and releases active TGF-β. Resultant active TGF-β induces hepatic fibrosis/cirrhosis and suppresses the growth of hepatic cells, namely, liver regeneration. The peptide of the present invention acts as a decoy against protease action on the aforementioned cleavage site, and competitively suppresses the TGF-β activation reaction, and thus is able to efficiently suppress formation of TGF-β-associated pathologic conditions.

BEST MODE FOR CARRYING OUT THE INVENTION

Figure 1:
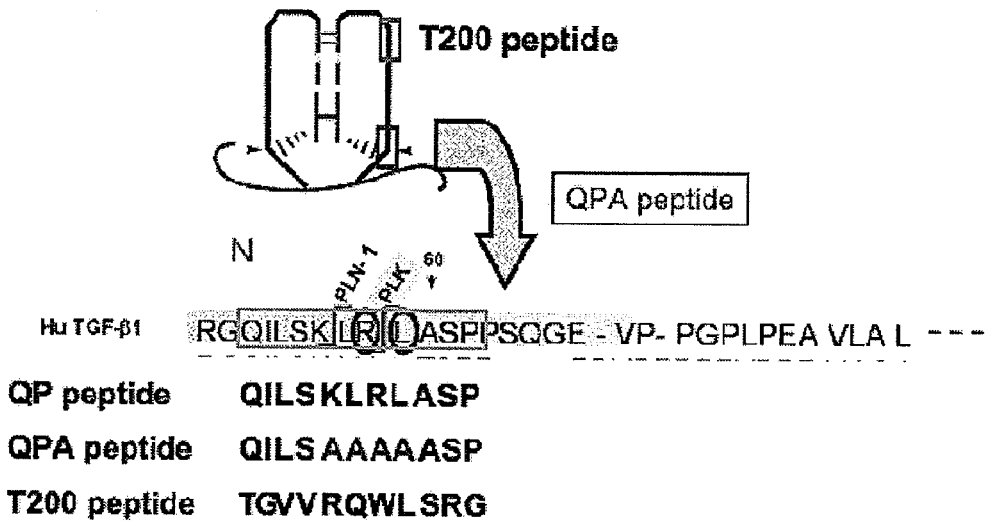
FIG. 1 shows sequences of the QP (SEQ ID NO: 47), QPA (SEQ ID NO: 48), and T200 (SEQ ID NO: 49) peptides, as well as residues 19-49 of SEQ ID NO: 6 (Hu TGF-β1).

The embodiments of the present invention will be described in detail below.

Transforming growth factor (TGF)-β is a multifunctional, homodimeric cytokine with a molecular weight of 25 kD, and exhibits a variety of biological activities.—e.g It plays a role in the pathogenesis of numerous types of sclerotic diseases, rheumatoid arthritis, and proliferative vitreoretinopathy. It is deeply involved in epilation and suppresses the functions of immune cells. On the other hand, TGF-β suppresses excessive generation of proteases, so as to prevent lung tissues from degradation and resulting in emphysema, as well as the growth of cancer cells. In human, TGF-β has three isoforms, TGF-β1~TGF-β3. TGF-β is generated as an inactive latent form with a molecular weight of approximately 300 kD, which is not able to bind to a receptor, and get activated on the surface of a target cell or its periphery thereof, so that it becomes an active form capable of binding to a receptor and thus exhibits its biological activities thereof.

The action of TGF-β on a target cell is transduced via a series of phosphorylation reactions of the signal transducing proteins known as Smads. When active TGF-β binds to a type II TGF-β receptor on a target cell surface, a receptor complex consisting of two molecule each of type II TGF-β receptor and type I TGF-β receptor is formed, and the type II receptor then phosphorylates the type I receptor. Subsequently, the phosphorylated type I receptor phosphorylates Smad2 or Smad3, and the phosphorylated Smad2 or Smad3 then forms a complex with Smad4. The complex moves into the nucleus, binds to a target sequence known as CAGA box existing in a target gene promoter region, and together with a coactivator, induces the expression of the target gene at a transcription level.

The present inventors have discovered that latent TGF-β is proteolytically cleaved and activated by proteases in the liver, and that the resultant active TGF-β induces fibrogenesis and suppresses the growth of hepatic cells, thereby causing hepatic fibrosis/cirrhosis and impaired liver regeneration respectively. Thus, the inventors have reported that the pathogenesis of hepatic fibrosis/cirrhosis as well as impaired liver regeneration can be suppressed by inhibiting the TGF-β activation reaction using a protease inhibitor (Okuno M et al., Gastroenterology 2001, 120: 1784-1800; Akita K et al., Gastroenterology 2002, 123: 352-364). Based on these findings, the inventors have reported a therapy using an antibody against protease (JP Patent Publication (Kokai) No. 2003-252792 A). Subsequently, with the anticipation that a synergistic effect could be obtained in suppressing the aforementioned pathogenesis by combinational use of an inhibitor suppressing TGF-β signal transduction and a protease inhibitor suppressing TGF-β activation, the present inventors screened an inhibitor of TGF-β signal transduction, discovered cytoxazone having an oxazolidinone ring, and reported a method to treat and/or prevent TGF-β-related diseases based on inhibition of TGF-β signal transduction pathway using cytoxazone (International Publication WO2005/039570).

Moreover, the present inventors have found that during the proteolytic TGF-β activation reaction, plasmin and plasma kallikrein, respectively, cleaved between Lys56 and Leu57 and between Arg58 and Leu59 within LAP (latency associated protein) sequence located at N-terminal portion of the latent TGF-β1 molecule, and also succeeded in producing antibodies that specifically recognize each cleaved section, namely, antibodies detecting pathogenesis-, tissue-, and isoform-specific TGF-β activation reactions International Publication WO2005/023870). In the present invention, the inventors have confirmed that generation of active TGF-β can be stably suppressed via competitive inhibition in the plasmin/plasma kallikrein-dependent TGF-β activation reaction with low concentrations of all the synthetic peptides derived from 11 amino acid sequence in a latent TGF-β1 molecule ranging from Gln52 to Pro62 and including both the plasmin cleavage site, Lys56 and Leu57, and the plasma kallikrein cleavage site, Arg58 and Leu59 (hereinafter referred to as QP peptide) as well as their mutant peptides having substitution of all of Lys56, Leu57, Arg58 and Leu59 with Ala (hereinafter referred to as QPA peptide) or Gln (hereinafter referred to as a QPQ peptide) so as to avoid cleavage by proteases, resulting in suppression of the pathogenesis of liver diseases. Thus, the inventors have established a platform for developing a novel method to cure and/or prevent TGF-β-related diseases based on specific inhibition of the TGF-β activation reaction.

The peptides of the present invention are those consisting of 11 to 50 amino acid residues, which comprise an amino acid sequence, Gln-Ile-Leu-Ser-X1-X2-X3-X4-Ala-Ser-Pro (SEQ ID NO: 1). In the aforementioned formula, each of X1 to X4 independently represents any given amino acid residue. Such any given amino acid residues include 20 types of natural amino acids (glycine, alanine, valine, leucine, isoleucine, serine, threonine, aspartic acid, glutamic acid, asparagine, glutamine, lysine, arginine, cystine, methionine, phenylalanine, tyrosine, histidine, tryptophan, and proline). However, X1-X2-X3-X4 is a sequence, which is not Lys-Leu-Arg-Leu (SEQ ID NO: 12), and is not cleavable by proteases.

In order to make the peptides of the present invention more resistant to the activation by TGF-β-activating proteases, X1 and X3 are preferably amino acid residues other than basic amino acids. Herein, basic amino acids mean lycine, arginine, and histidine.

The lengths of the peptides of the present invention are not particularly limited, as long as they consist of 11 to 50 amino acid residues. The length of the present peptide is preferably 11 to 30 amino acid residues, more preferably 11 to 20 amino acid residues, further more preferably 11 to 15 amino acid residues, and particularly preferably 11 amino acid residues.

When the peptide of the present invention is longer than 11 amino acids, addition of an amino acid(s) is made to the N-terminal side and/or C-terminal side of the amino acid sequence, Gln-Ile-Leu-Ser-X1-X2-X3-X4-Ala-Ser-Pro (SEQ ID NO: 1). As amino acid sequences to be added, the amino acid sequences located within the N-terminal side and/or C-terminal side of the underlined amino acid sequences of TGF-β1, TGF-β2 and TGF-β3, which are shown below, and the portions thereof, can be selected. In case of TGF-β1, for example, to the N-terminal side of the amino acid sequence, Gln-Ile-Leu-Ser-X1-X2-X3-X4-Ala-Ser-Pro (SEQ ID NO: 1), the following amino acid sequence portion can be added: G, RG, IRG, AIRG (SEQ ID NO: 13), EAIRG (SEQ ID NO: 14), IEAIRG (SEQ ID NO: 15), RIEAIRG (SEQ ID NO: 16), KRIEAIRG (SEQ ID NO: 17), RKRJEAIRG (SEQ ID NO: 18), KRKRIEAIRG (SEQ ID NO: 19), VKIRKRIEAIRG (SEQ ID NO: 20), LVKRKRIEAIRG SE ID NO: 21), ELVKRKRIEAIRG SE ID NO: 22), MELVKRKRIEAIRG (SEQ ID NO: 23), DMELVKRKRIEAIRG (SEQ ID NO: 24), IDMELVKRKRIEAIRG (SEQ ID NO: 25), TIDMELVKRKRIEAIRG (SEQ ID NO: 26), KTIDMELVKRKRIEAIRG (SEQ ID NO: 27), CKTIDMELVKRKRIEAIRG (SEQ ID NO: 28), and TCKTIDMELVKRKRIEAIRG (SEQ ID NO: 29). Likewise, in case of TGF-β1, to the C-terminal side of the amino acid sequence, Gln-Ile-Leu-Ser-X1-X2-X3-X4-Ala-Ser-Pro (SEQ ID NO: 1), the following amino acid sequence portions can be added: P, PS, PSQ, PSQG (SEQ ID NO: 30), PSQGE (SEQ ID NO: 31), PSQGEV (SEQ ID NO: 32), PSQGEVP (SEQ ID NO: 33), PSQGEVPP (SEQ ID NO: 34), PSQGEVPPG (SEQ ID NO: 35), PSQGEVPPGP (SEQ ID NO: 36), PSQGEVPPGPL (SEQ ID NO: 37), PSQGEVPPGPLP (SEQ ID NO: 38), PSQGEVPPGPLPE (SEQ ID NO: 39), PSQGEVPPGPLPEA (SEQ ID NO: 40), PSQGEVPPGPLPEAV (SEQ ID NO: 41), PSQGEVPPGPLPEAVL (SEQ ID NO: 42), PSQGEVPPGPLPEAVLA (SEQ ID NO: 43), PSQGEVPPGPLPEAVLAL NO: 44 PSQGEVPPGPLPEAVLALY SE ID NO: 45 and PSQGEVPPGPLPEAVLALYN (SEQ ID NO: 46). Also in case of TGF-β2 and TGF-β3, amino acid sequence portions can be added in the same manner, based on the following amino acid sequences.

TGF-β1
(SEQ ID NO: 6)
(N-terminus)-TCKTIDMELVKRKRIFEIRG-<u>QILSKLRLASP</u>-PSQG

EVPPGPLPEAVLALYN-(C-terminus)

TGF-β2
(SEQ ID NO: 7)
(N-terminus)-TCSTLDMDQFMRKRIEAIRG-<u>QILSKLKLTSP</u>-PEDY

PEPEEVPPEVISIYNS-(C-terminus)

TGF-β3
(SEQ ID NO: 8)
(N-terminus)-TCTTLDFGHIKKKRVEAIRG-<u>QILSKLRLTSP</u>-PEPT

VMTHVPYQVLALYNST-(C-terminus)

The types of amino acid residues comprised in the peptide of the present invention are not particularly limited. The aforementioned amino acid residues may be natural amino acid residues, non-natural amino acid residues, and their derivatives. That is to say, as amino acids, either L-amino acids or D-amino acids may be used. Otherwise, a mixture thereof may also be used. In addition, with regard to the type of amino acid, any one of α-amino acid, β-amino acid, γ-amino acid, and δ-amino acid may be used. Of these, α-amino acid as a natural amino acid is preferable.

The term "non-natural amino acid" is used in the present specification to mean all amino acids other than 20 types of natural amino acids that constitute of natural proteins (glycine, L-alanine, L-valine, L-leucine, L-isoleucine, L-serine, L-threonine, L-asparatic acid, L-glutamic acid, L-asparagine, L-glutamine, L-lycine, L-arginine, L-cystine, L-methionine, L-phenylalanine, L-tyrosine, L-tryptophan, L-histidine, and L-proline). Specific examples of such a non-natural amino acid include: (1) non-natural amino acids formed by substituting atoms contained in natural amino acids with other substances; (2) optical isomers on the side chains of natural amino acids; (3) non-natural amino acids formed by introducing substituents into the side chains of natural amino acids; and (4) non-natural amino acids formed by substitution of the side chains of natural amino acids so as to change hydrophobicity, reactivity, charge state, molecular size, hydrogen bond ability, etc.

The term "derivative" of an amino acid is used in the present invention to mean an amino acid derivative subjected to chemical modification, biological modification, etc. Examples of such modification include, but not limited to: functional group transformation caused by introduction of a functional group (such as alkylation, esterification, halogenation or amination), oxidation, reduction, addition or dissociation; and introduction of a sugar compound (monosaccharide, disaccharide, oligosaccharide or polysaccharide) or a lipid compound; phosphorylation; or biotinylation.

The aforementioned peptides of the present invention may be in a free form, or may also be provided in the form of an acid-added salt or a base-added salt. Examples of such an acid-added salt include: mineral salts such as hydrochloride, sulfate, nitrate or phosphate; and organic acid salts such as p-toluenesulfonate, methanesulfonate, citrate, oxalate, maleate or tartrate. Examples of such a base-added salt include: metal salts such as a sodium salt, a potassium salt, a calcium salt or a magnesium salt; ammonium salts; and organic ammonium salts such as a methylammonium salt or a triethylammonium salt. There may be a case where the aforementioned peptide forms a salt together with an amino acid such as glycine. There may also be a case where it forms a counterion in a molecule.

Moreover, there may also be a case where the aforementioned peptide or a salt thereof exists in the form of a hydrate or a solvate. The aforementioned peptide has multiple asymmetric carbon atoms. The form of each asymmetric carbon atom is not particularly limited. An amino acid residue is preferably an L-amino acid. Optically active substances based on such asymmetric carbon atoms, stereoisomers such as a diastereoisomer, any given mixture of stereoisomers, a racemic body, etc. are all included in the scope of the present invention.

The peptide of the present invention can be synthesized by ordinary methods known to persons skilled in the art. Examples of such ordinary methods include an azide method, an acid chloride method, an acid anhydride method, a mixed acid anhydride method, a DCC method, an active ester method, a carboimidazole method, and an oxidation-reduction method. In addition, either a solid-phase synthesis method or a liquid-phase synthesis method may be applied to the aforementioned synthesis. That is to say, amino acids capable of constituting the peptide of the present invention and the remaining portion are condensed, and when the thus generated product has a protecting group, such a protecting group is dissociated, so as to synthesize the peptide of interest. As a condensation method or a method of dissociating a protecting group, any types of known methods may be applied [please refer to Bodanszky, M and M. A. Ondetti, Peptide Synthesis, Interscience Publishers, New York (1966), Schroeder and Luebke, The Peptide, Academic Press, New York (1965), and Nobuo Izumiya et al., *Peptide Gosei no Kiso to Jikken* (Bases and Experiments for Peptide Synthesis), Maruzen (1975), for example].

After completion of the reaction, the peptide of the present invention can be purified by the combined use of ordinary purification methods such as solvent extraction, distillation, column chromatography, liquid chromatography, and recrystallization. In addition, the C-terminus of the peptide of the present invention is generally a carboxyl (—COOH) group or a carboxylate (—COO$^-$). However, the aforementioned C-terminus may also be an amide (—CONH$_2$) or an ester (—COOR). Herein, R in such an ester may be an alkyl group containing 1 to 12 carbon atoms, a cycloalkyl group containing 3 to 10 carbon atoms, an aryl group containing 6 to 12 carbon atoms, an aralkyl group containing 7 to 12 carbon atoms, or the like. Moreover, the peptide of the present invention includes a peptide, an amino group of the N-terminus of which is protected by a protecting group, and a complex peptide such as a glycopeptide to which a sugar chain binds.

Another method for producing the peptide of the present invention is a method for producing the peptide of the present invention in host cells such as microorganism cells, plant cells, or animal cells in the form of a recombinant protein (peptide) by a genetic engineering means using a gene that encodes the amino acid sequence of the peptide of the present invention. The obtained recombinant peptide can be purified by common means used in purification of proteins or peptides, such as gel filtration, reverse phase HPLC, or ion exchange column purification.

Since the peptide shown in the present invention exhibits the activity to block generation of active TGF-$\beta$, it can be used as a TGF-$\beta$ generation suppressing agent. In addition, the peptide of the present invention, which exhibits the activity to block generation of active TGF-$\beta$, can be used as a medicament for treating and/or preventing any pathogenesis associated with TGF-$\beta$. Thus, the peptide of the present invention can be used as a liver regeneration promoting agent or a hepatic fibrosis-suppressing agent, for example. The TGF-$\beta$-associating pathologic conditions include diseases attended with the fibrosis of tissues (lung, liver, kidney, skin, etc.). Specific examples of such diseases attended with the fibrosis of tissues include lung fibrosis, hepatic cirrhosis, renal disease (nephritis, nephrosclerosis), vascular restenosis, arteriosclerosis, psoriasis, scleroderma, atopy, keloid, and arthritis.

Moreover, the peptide of the present invention can be used as a medicament, directly or in the form of a mixture produced by mixing the present peptide into various types of solid carriers, liquid carriers, emulsifying and dispersing agents, etc., which are commonly used in the field of manufacturing pharmaceutical formulations. Specifically, when the peptide of the present invention is used in the form of a pharmaceutical composition, the dosage form can be selected, as appropriate, depending on a usage or a target to which the pharmaceutical composition is to be used. For example, the aforementioned pharmaceutical composition can be used in the form of a tablet, a pill, a powder, a liquid agent, a suspension, an emulsion, a granule, a capsule, a suppository, an injection (in the case of a liquid agent, a suspension, etc.), and the like.

Examples of a carrier that can be used for the formation of a tablet include: excipients such as lactose, sucrose, sodium chloride, glucose, urea, starch, calcium carbonate, kaoline, crystalline cellulose, or silicic acid; binders such as starch impregnated with water or alcohols, gelatin, carboxymethylcellulose sodium (CMC-Na), methylcellulose (MC), hydroxypropylcellulose (HPC), hydroxypropylmethylcellulose (HPMC), calcium phosphate, or polyvinylpyrrolidone; disintegrators such as dry starch, agar powder, laminaran powder, sodium bicarbonate, calcium carbonate, polyoxyethylene sorbitan fatty acid esters, sodium lauryl sulfate, monoglyceride stearate, starch, or lactose; disintegration regulators such as sucrose, stearin, cacao butter, or hydrogenated oil; adsorbents such as a quaternary ammonium base, sodium lauryl sulfate, or colloidal silica; and lubricants such as purified talc, stearate, boric acid powder, or polyethylene glycol. Furthermore, as necessary, such a tablet may also be converted to a tablet coated with a common tablet coat, such as a sugar-coated tablet, a gelatin-coated tablet, an enteric-coated tablet, a double layer tablet, or a multilayer tablet.

Further, when the peptide of the present invention is prepared in the form of an injection, it is preferable that a liquid agent, an emulsion, and a suspension be sterilized, and be isotonic with blood. In order to process the peptide of the present invention into such a form, water, ethyl alcohol, propylene glycol, ethoxylated isostearyl alcohol, polyoxylated isostearyl alcohol, polyoxyethylene sorbitan fatty acid esters, etc. can be used as diluents. In addition, as necessary, stabilizers such as sodium bisulfite or sodium pyrosulfife, suspending agents such as carboxymethyl cellulose, sodium alginate or aluminum monostearate, isotonizing agents such as sodium chloride, glucose or glycerin, preservatives such as p-hydroxybenzoic esters, benzyl alcohol or chlorobutanol, solubilizing agents, buffers, soothing agents, etc. may be mixed and used.

Moreover, commonly used coloring agents, aromatics, flavoring agents, sweeteners, etc. may also be mixed into the pharmaceutical compositions of the aforementioned various embodiments, as necessary. Furthermore, other pharmaceutical active ingredients may also be mixed therein. When the peptide of the present invention is used as a medicament, the aforementioned peptide may be comprised at a ratio generally between 0.001% and 90% by weight, and preferably between 0.001% and 80% by weight, in the aforementioned medicament.

The peptide of the present invention may be administered to mammals including a human. As an administration route, either oral administration or parenteral administration may be adopted. The dose of the peptide of the present invention may be appropriately increased or decreased, depending on conditions such as the age, sex or body weight of a patient, symptoms, or an administration route. The amount of the active ingredient thereof is generally between approximately 1 µg/kg and 1,000 mg/kg, and preferably between approximately 10 µg/kg and 100 mg/kg, per adult per day. The aforementioned dose may be administered once or divided over several administrations per day. Moreover, an administration period and an administration interval are not particularly limited, either. The peptide of the present invention may be administered every day or at intervals of several days.

The present invention will be more specifically described in the following examples. However, these examples are not intended to limit the scope of the present invention.

EXAMPLES

Example 1

Suppression of the Activation of Hepatic Stellate Cells by QP and QPA Peptides

According to the method previously reported (Okuno M. et al., Gastroenterology 2001; 120: 1784-1800), hepatic stellate cells were isolated from the liver of male Wistar rats (body weight: 350 to 400 g; Japan Clea), and the isolated cells were then seeded in a concentration of $1 \times 10^6$ cells/dish on a 3.5-cm culture plastic dish. Thereafter, the cells were cultured in 1 ml of Dulbecco's modified Eagle medium (DMEM; manufactured by SIGMA) containing 10% fetal calf serum (FCS; manufactured by GIBCO).

From day one of isolation of hepatic stellate cells, they were cultured for 7 days with the following peptides added in the medium; QP peptide (Gln-Ile-Leu-Ser-Lys-Leu-Arg-Leu-Ala-Ser-Pro) (SEQ ID NO: 9); QPA peptide (Gln-Ile-Leu-Ser-Ala-Ala-Ala-Leu-Ala-Ser-Pro) (SEQ ID NO: 10); and a control synthetic peptide consisting of 11 amino acids that is derived from a latent TGF-β1 LAP sequence (Thr-Gly-Val-Val-Arg-Gln-Trp-Leu-Ser-Arg-Gly; this is referred to as T200 peptide) (SEQ ID NO: 11) (please refer to FIG. 1), however anticipated not to influence TGF-β activation reaction because of the sequence being apart from the TGF-β activation control region (Gly51 to Arg110) discovered by the present inventors (International Publication WO2005/023870). The control peptide sequence is also selected so as not to include common cleavage sequences for serine proteases or matrix metalloproteinases known to possess the activity to activate latent TGF-β Kondo et al., *Nihon Kessen Shiketu Gakkaishi* (the Bulletin of the Japanese Society on Thrombosis and Hemostatis), 2003, 14: 210-219; Annes et al., J Cell Sci 2003, 116: 217-224). Influence of each peptide on transformation of hepatic stellate cells (which is also referred to as activation of hepatic stellate cells) induced by culturing them on the plastic dish was observed under a microscope.

A 60 mM aqueous stock solution of each peptide was prepared, and the peptide was then dissolved in a medium to make a final concentration of 1 mM. Until the $3^{rd}$ day of isolation, the aforementioned cells were treated in a DMEM medium containing 10% FCS. On the $4^{th}$ day, the medium was exchanged with serum free DMEM containing 0.1% bovine serum albumin (BSA) and each peptide with a final concentration of 1 mM, and the culture was further continued for 2 to 4 days. Thereafter, the culture medium was collected as a conditioned medium, and the amount of active TGF-β1 present in the conditioned medium was measured using an ELISA kit manufactured by PROMEGA. At the same time, the state of the cells was observed under a microscope (DMIRB; manufactured by Leica) and was then photographed.

Figure 2:
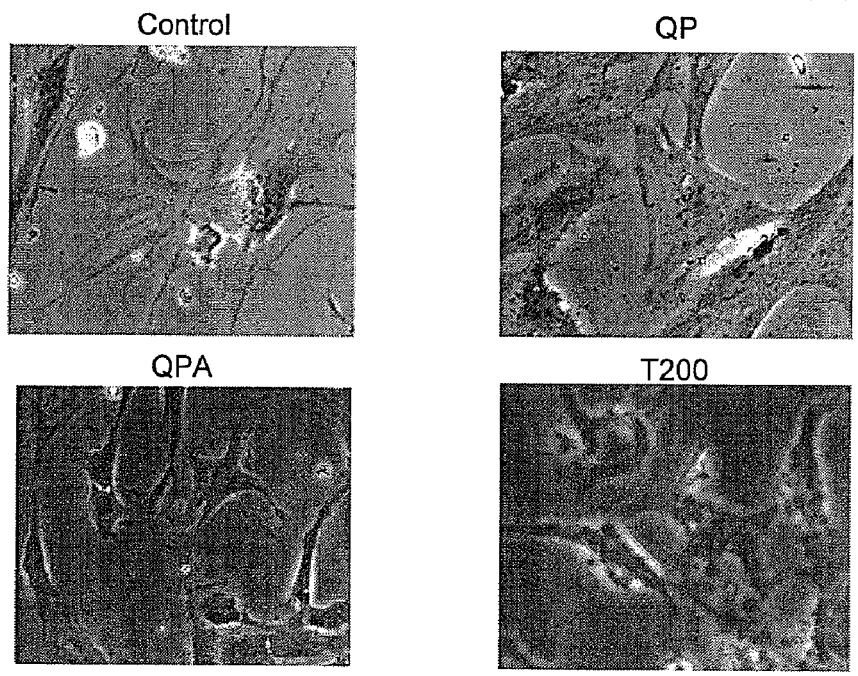
FIG. 2 shows suppression of hepatic stellate cell activation with peptides derived from latent TGF-β sequence containing proteolytic cleavage sites.

FIG. 2 shows the results of the observation under a microscope. As shown in FIG. 2, the QPA peptide significantly suppressed the activation of hepatic stellate cells (a morphological change attended with the disappearance of vitamin A-containing oil droplets). On the other hand, the QP peptide exhibited a weakly suppressing effect, and the T200 peptide did not exhibit such a suppressing effect.

Next, Table 1 shows the results of measuring the amount of active TGF-β generated into the conditioned medium. As shown in Table 1, the QPA peptide significantly reduced the amount of active TGF-α generated into the conditioned medium to 1/55 (2%) of the control. In contrast, the T200 peptide, which did not show a significant stellate cell activation-suppressing activity, reduced the amount of active TGF-β generated into the conditioned medium to 74% of the control.

TABLE 1

Suppression of active TGF-β generation attended with activation of hepatic stellate cells by peptides derived from TGF-β-activating protease cleavage sequences

|  | TGF-β (pg/ml) |
| --- | --- |
| Control | 217 ± 66 |
| QPA peptide | 4 ± 1* |
| T200 peptide | 160 ± 19 |

*$P < 0.01$

From the above results, it was found that the QPA peptide suppresses the TGF-β activation reaction by plasmin/plasma kallikrein, thereby suppressing activation of hepatic stellate cells.

Example 2

Improvement of Impaired Liver Regeneration by QP and QPA Peptides

Next, in vivo effects of the QP and OPA peptides were examined in endotoxin (LPS)-preadministered partially-hepatectomized mice model for impaired liver regeneration (Akita K. et al., Gastroenterology 2002, 123: 352-364), in which impaired liver regeneration has been demonstrated to be induced due to plasma kallikrein-dependent TGF-β activation reaction.

For the experiment, 26 five-week-old male C3H/HeN mice were used. After completion of quarantine and environmental acclimatization, the mice were divided into the following 5 groups according to the body weight of each mouse on the day of grouping. These include, a group to which saline was preadministered and saline was then administered (G1: n=6); a group to which LPS was preadministered and saline was then administered (G2: n=6); a group to which LPS was preadministered and QP peptide was then administered (G3: n=4); a group to which LPS was preadministered and QPA peptide was then administered (G4: n=4); and a group to which LPS was preadministered and T200 peptide was then administered (G5: n=6) (Table 2).

After starting the test, 7 μg of LPS (saline in the case of G1) was intraperitoneally administered. Forty-eight hours later, partial hepatectomy was carried out on all the mice. Another forty-eight hours later, all the surviving mice were subjected to an autopsy. In the autopsy, blood was collected. Thereafter, 1 to 3 mice from each group were subjected to systemic perfusion with 4% paraformaldehyde (PFA), and the liver was then excised. All the excised lobes were embedded in an embedding agent "Tissue Mount" in a frozen state. On the other hand, the remaining 1 to 3 mice from each group were not subjected to systemic perfusion, and a portion of the liver was fixed with formalin, and the remaining portion was collected to be used as a frozen sample (used for mRNA and for protein quantitation). The organ that had been fixed with formalin was processed into a block, and it was then preserved together with the frozen sample in a deep freezer at −80° C.

The following test materials and method were applied.

1. Inducer 1.1 Inducer

Name: Lipopolysaccharides (LPS; from *Escherichia coli* 0111: B4) (manufactured by SIGMA)

Preservation method: cold storage, shaded, and hermetically sealed 1.2 Solvent

Name: Sterilized saline (manufactured by Otsuka Pharmaceutical Co., Ltd.)

2. Test substance 2.1 QP peptide

Name: TGF-β1 LAP peptide

Amino acid sequence: N-52QILSKLRLASP62-C (SEQ ID NO: 47)

Preservation method: cold storage 2.2 QPA peptide

Name: TGF-131 LAP peptide (a mutant peptide of N-52QJL-SKLRLASP62-C (SEQ ID NO: 47))

Amino acid sequence: N-52QILSAAAAASP62-C (SEQ ID NO: 48)

Preservation method: cold storage 2.3 T200 peptide

Name: TGF-f31 LAP peptide (a peptide corresponding to a portion that is not associated with an activation reaction)

Amino acid sequence: N-200TGVVRQWLSRG210-C (SEQ ID NO: 49)

Preservation method: cold storage

3. Animal Subjected to the Test

Animal species: mouse

Strain: C3H/HeN Slc

Supplier: Japan SLC, Inc., Shizuoka

Microbiological variety: Specific Pathogen Free (SPF)

Sex: male

Age in week: 5 weeks old when introduced (6 weeks old when subjected to the test)

TABLE 2

Constitution of test groups

| Group name | Number of mice | Inducer (i.p.) | Sample administered (i.v.) | Systemic perfusion | Mouse No. |
|---|---|---|---|---|---|
| G1 | 6 | Saline | Saline 100 μL/head | Yes | M001 to M003 |
|  |  |  |  | No | M004 to M006 |
| G2 | 6 | LPS 7 μg/head | Saline 100 μL/head | Yes | M007 to M009 |
|  |  |  |  | No | M010 to M012 |
| G3 | 4 | LPS 7 μg/head | QP peptide | Yes | M013 and M014 |
|  |  |  | 200 μg/100 μL/head/time | No | M015 and M016 |
| G4 | 4 | LPS 7 μg/head | QPA peptide | Yes | M017 and M018 |
|  |  |  | 200 μg/100 μL/head/time | No | M019 and M020 |
| G5 | 6 | LPS 7 μg/head | T200 peptide | Yes | M021 to M023 |
|  |  |  | 200 μg/100 μL/head/time | No | M024 to M026 |

4. Breeding and Control of Animals

The introduced animals were allowed to be acclimatized in a new breeding environment. At the same time, the state of the animals was observed every day by confirming it from outside the cage. Thus, it was confirmed that mice were constantly in a good condition.

Breeding period: 5 days after introduction

Test period: 8 days

5. Grouping of the Animals to be Subjected to the Test 5.1 Grouping Timing: 7 Days after Introduction of the Animals 5.2 Grouping Method Taking into consideration the body weights of the animals 5 days after the introduction, a grouping system, Statlight #11 Grouping (Yukms Co., Ltd., Tokyo) was used to conduct grouping according to a completely random method.

5.3 Discrimination of Cages

A label, on which group name, test number, strain name, the name of an analyte to be administered, the presence or absence of perfusion, mouse number, introduction number, and cage number were clearly described, was attached to each cage.

6. Discrimination of Animals

After completion of the grouping, animals were individually bred. Since discrimination was carried out among cages, discrimination was not carried out among individual mice.

7. Administration of Inducer 7.1 Preparation of LPS-Administering Sample

Preparation frequency: once (on site preparation)

Preparation method: A small amount of saline was added to one vial container that contained 5 mg of LPS, and it was then dissolved therein. Subsequently, the resultant solution was transferred into another container, and saline was then gradually added thereto to a total amount of 5 mL. The thus obtained solution was defined as a 1 μg/μL solution. 350 μL was collected from the obtained solution by precise weighing, and it was then added to a container that contained 4.65 mL of a sterilized normal saline solution (solvent). Thereafter, the mixed solution was filtrated and sterilized using a 0.22-μm filter, and the resultant was used as a sample to be administered.

7.2 LPS Administration Method

Dose: 7 μg/head

Administration route: intraperitoneal administration

Administration volume: 0.1 mL/head

Administration number: once (single administration)

Administration timing: 48 hours before partial hepatectomy

Target animal: G2 to G5 (To G1, saline was administered.)

8. Administration of Test Substance 8.1 Preparation of Peptide-Administering Sample Preparation frequency: once Preparation method: A peptide was dissolved in saline to a concentration of 2 mg/ml, and the resultant was used as a sample to be administered.

Preservation method: The sample was preserved in a refrigerator before use. (The temperature was set at 4° C.)

8.2 Peptide Administration Method

Dose: 200 μg/head

Administration route: intravenous administration

Administration volume: 0.11 mL/head

Administration timing: 50, 38, 24, 14 and 2 hours before, and 10, 24 and 34 after partial hepatectomy Number of administration: twice/day, for 4 days (in principle, at 9:00 and at 19:00), 8 times in total Target animal: G2 to G5 (To G1 and G2, saline was administered.)

9. Partial Hepatectomy (⅔ Partial Hepatectomy; PH)

9.1 Treating Method

Each mouse was subjected to inhalation anesthesia with diethyl ether, and the hair ranging from the thorax to the abdomen was shaved. The mouse was immobilized on an autopsy table on its back, and the skin at a surgical site was disinfected with Isodine. The abdomen was excised. Through the excised portion, the hepatic external left lobe, internal right lobe, and internal left lobe were removed from the body, and their roots were bound with a thread. The thus removed liver was cut off. The blood was wiped away, and the opened abdomen was then closed with a staple. The treatment was terminated by disinfecting the skin with Isodine.

9.2 Number of Mice Treated: All the 26 Mice 9.3 Treating Timing: 48 Hours after Administration of LPS 10. Observation of General Condition and Measurement of Body Weight 10.1 Observation of General Condition After initiation of the test, general conditions of all the mice were observed once a day. When abnormity was observed, the details thereof were recorded.

10.2 Measurement of Body Weight

After initiation of the test, the body weights of all the mice were measured once a day or more, and the recorded paper printed paper) was conserved, and the obtained data was then aggregated.

11. Autopsy 11.1 Autopsy Timing: 48 Hours after Partial hepatectomy (PH)

11.2 Autopsy Method

Pentobarbital sodium at a dose of 40 mg/kg was intraperitoneally administered to the mice, so that they were then anesthetized. Thereafter, using an untreated syringe, as large amount as possible of blood was collected from the abdominal aorta, so as to cause death to the mice due to exsanguination.

After completion of the blood collection, 1 to 3 mice from each group were subjected to systemic perfusion with 4% PFA, and the liver was then excised from each mouse. All the excised lobes were embedded in an embedding agent "Tissue Mount" in a frozen state. On the other hand, the remaining 1 to 3 mice from each group were not subjected to systemic perfusion, and a portion of the liver was fixed by immersing it in a 10% neutral buffer formalin solution, and the remaining portion was frozen with liquid nitrogen and it was preserved in the form of a frozen sample (used for mRNA and for protein quantitation).

11.3 Treatment of Blood

The blood was centrifuged within 1 hour after blood collection at 3,000 r.p.m. for 10 minutes, while cooling (the temperature was set at 4° C.). The serum fraction was collected in another container, and it was preserved in a frozen state (the temperature was set at −80° C.).

12. Preparation of Histopathological Specimen

Prepared organ: liver

Prepared specimen: paraffin block

Preparation method: After fixing with a 10% neutral buffer formalin solution, the liver was excised, and it was then subjected to dehydration and paraffin embedding according to an ordinary method.

13. Preparation of Tissue Section and Staining Thereof.

Using a rotary microtome (Leica), a hepatic tissue section with a thickness of 5 μm was prepared from the embedded hepatic tissues. A proliferating cell nuclear antigen (PCNA; a proliferating cell marker) was stained according to the previously reported method (Greenwell A. et al., Cancer Lett 1991; 59: 251-256) using a Histofine kit (Nichirei Corporation). That is to say, paraffin was removed from the hepatic tissue section, and the section (thickness: 5 μm) was stained by the following operations in accordance with instructions included with the kit.

incubation with a citrate buffer (pH 6) in a water bath of 95° C. for 10 minutes;

incubation with a 3% hydrogen peroxide water at room temperature for 20 minutes; (hereafter, in a humidifier chamber, at room temperature)

incubation with a blocking buffer included with the kit for 60 minutes;

incubation with a stock solution of a mouse anti-rat PCNA monoclonal antibody (manufactured by Dako) for 10 minutes (primary antibody);

incubation with a blocking buffer included with the kit for 10 minutes;

incubation with Simple Stain Mouse MAX-PO (M) included with the kit for 10 minutes (secondary antibody); and incubation with a mixed solution of diaminobenzidine tetrahydrochloride (DAB) (manufactured by Vector) for 4 minutes 30 seconds, so as to develop color.

Washing with PBS was carried out 3 times at intervals of the aforementioned operations.

The resultant was incubated with a hematoxylin solution (Muto Pure Chemicals) for 20 seconds and then with a sodium tetraborate solution, and counter staining was performed on the nucleus, followed by washing with filtrated Milli-Q water.

Using a DMIRB microscope manufactured by Leica, the obtained product was observed at a magnification of 200×, and it was then photographed. At the same time, the percentage of PCNA positive cells in each specimen was evaluated with n=8.

14. Measurement of Amount of TGF-β1 in Hepatic Tissues

A liver extract was prepared from approximately 100 mg of the hepatic tissues prepared for the use in protein quantitation in 11.2 above, according to the method of Okuno M. et al. (Okuno M. et al., Gastroenterology 2001; 120: 1784-1800). The amount of TGF-β1 in the extract was quantitated using an ELISA kit manufactured by PROMEGA. The quantitated TGF-β1 amount was presented as a pg/mg of protein.

(Results of Observation of General Condition)

In the LPS-administered groups, a decrease in autonomic movement and piloerection were confirmed at the observation conducted 12 hours after the administration of LPS. Thereafter, as the time passed, such symptoms were gradually recovered, and were then completely recovered before the PH treatment. After the mice were subjected to the PH treatment, symptoms such as a crouching position, a decrease in automatic movement, a decrease in the body temperature, and a hunchback position were observed in several mice. The death of several mice was also observed. It is considered that the aforementioned symptoms were caused by the PH treatment.

(Results of Staining)

Figure 3:
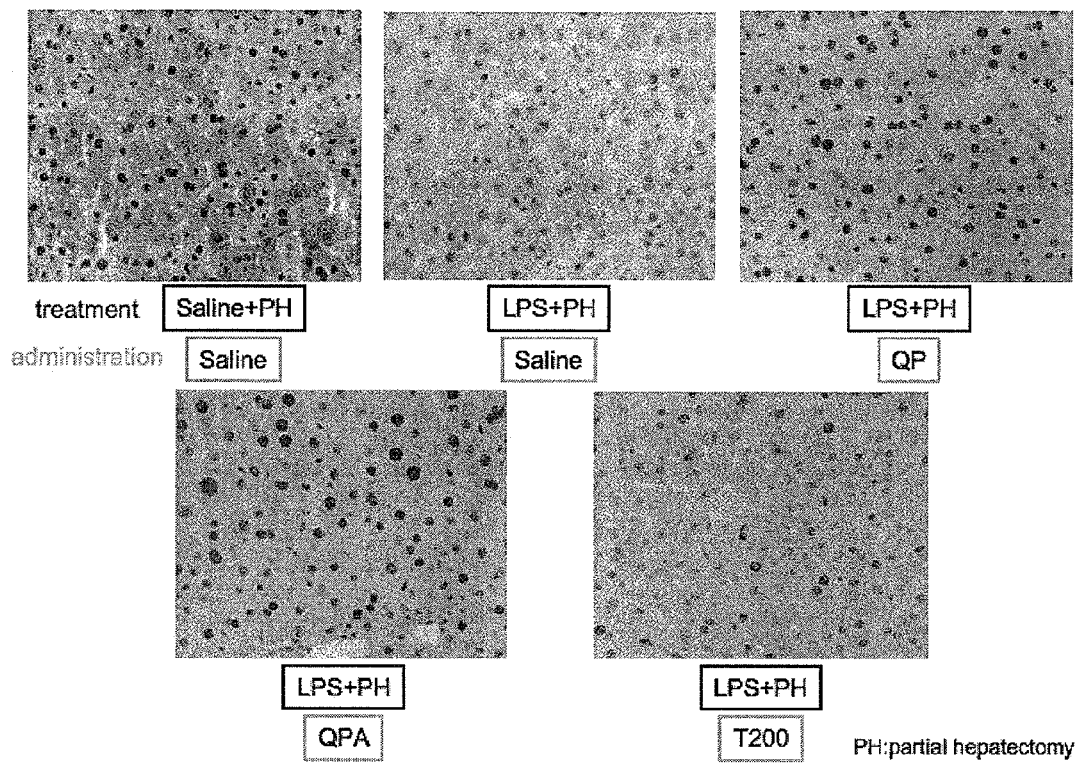
FIG. 3 shows the improvement of impaired liver regeneration with peptides derived from latent TGF-β sequence containing proteolytic cleavage sites (photographs)

The results of staining are shown in FIG. 3. By administering QP or QPA peptide to the mice, impaired liver regeneration due to preadministration of LPS was significantly improved (it had been demonstrated that impaired liver regeneration is caused by a plasma kallikrein-dependent TGF-β activation reaction). In contrast, T200 peptide did not exhibit such an improving effect.

(Results of Quantitation)

Figure 4:
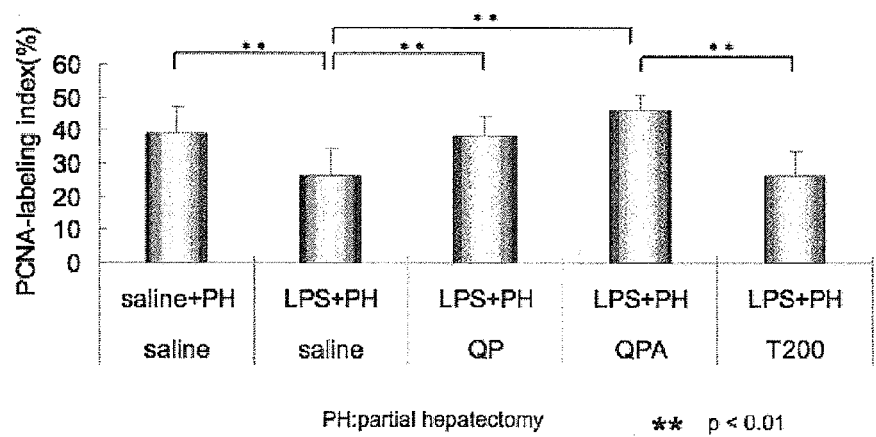
FIG. 4 shows the improvement of impaired liver regeneration with peptides derived from latent TGF-β sequence containing proteolytic cleavage sites (quantitation)

FIG. 4 shows the results of quantitating the aforementioned staining results with the percentage of PCNA positive hepatic cells. As a result of administration of the QP peptide to the mice, the percentage of impaired liver regeneration induced by preadministration of LPS (the percentage of PCNA positive cells was reduced from 40% to 25%, and it had been demonstrated that this is because of a plasma kallikrein-dependent TGF-β activation reaction; Akita et al., Gastroenterology 123: 352-364, 2002) was completely improved. Moreover, as a result of administration of the QPA peptide, the percentage of PCNA positive cells was increased to 47%, and thus the QPA peptide exhibited an impaired liver regeneration-improving effect and a liver regeneration-promoting effect. In contrast, the P200 peptide did not exhibited any such improving effects.

(Results of Quantitation of TGF-β1 Amount in Hepatic Tissues)

Table 3 shows the results of measuring the amounts of TGF-β1 generated in hepatic tissues. By preadministration of LPS, the hepatic contents of TGF-β1 increased approximately 6.5 times higher than the value of the control group. The QPA peptide prevented such an increase and kept the value to approximately 1.4 times higher than the value of the control group. In contrast, the T200 peptide only decreased the hepatic contents of TGF-β1 to approximately 3 times higher than the value of the control group.

TABLE 3

Suppression of TGF-β1 generation in hepatic tissues attended with impaired liver regeneration by peptides derived from TGF-β-activating protease cleavage sequences

| Treatment | Samples | Hepatic TGF-β1 Contents (pg/mg protein) | |
|---|---|---|---|
| Saline + PH (Control) | Saline | 7 ± 9 | |
| LPS + PH | Saline | 46 ± 4 | ] * |
| LPS + PH | QPA peptide | 10 ± 11 | |
| LPS + PH | T200 peptide | 20 ± 26 | |

*P < 0.05

(Summary and Consideration)

As stated above, it was demonstrated that low concentrations of both QP and QPA peptides, derived from the cleavage sequences of latent TGF-β1 LAP portions by TGF-β-activating proteases, suppress the proteolytic TGF-β activation reaction that causes liver diseases, inhibit generation of active TGF-β, and thus improve liver regeneration. The aforementioned effects of the QPA peptide are stronger than those of the QP peptide. This is considered to be because the QPA peptide is not cleaved by proteases, therefore stably and effectively exhibiting its inhibitory activity even when used at a low concentration. The result suggests that the QPA peptide may also block basic levels of TGF-β activation reaction endogenously occurring in a control. Using the present peptides, it becomes possible to stably inhibit the TGF-β activation reaction, which has been hardly achieved by prior art techniques. Thus, it can be anticipated that it will be possible to develop an agent for preventing and/or treating TGF-β-related diseases including various types of sclerotic diseases as typical examples by applying the present peptides and derivatives thereof.

Example 3

Inhibition of LAP Cleavage Reaction by QP and QPQ Peptides

Figures 5, 6:
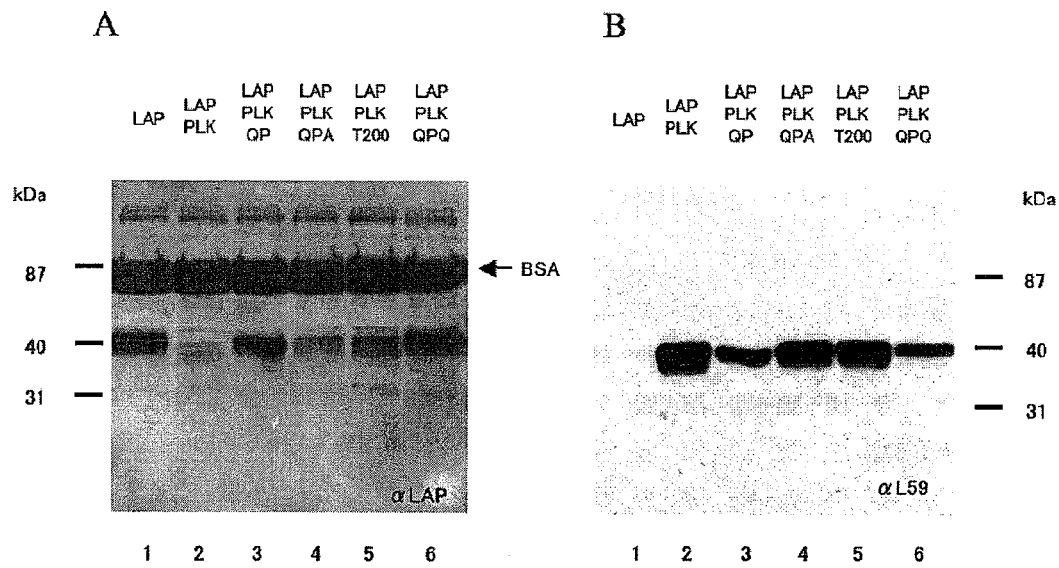
FIG. 5 shows the sequence of the QPQ peptide (SEQ ID NO: 50).
FIG. 6 shows inhibition of LAP cleavage reaction by the QP and QPQ peptides.

When 2 μg of recombinant human LAP R & D) (final concentration: 66 μg/ml) was incubated with plasma kallikrein (SIGMA; final concentration of 20 μg/ml), QP peptide, QPA peptide, T200 peptide, and QPQ peptide (SEQ ID NO: 4) were added thereto at a final concentration of 2.5 mg/ml, followed by incubation at 37° C. for 40 minutes. Thereafter, electrophoresis (room temperature, 27 mA, 50 minutes) was carried out using 13.5% polyacrylamide gel, so as to separate LAP (molecular weight: 41 kDa), a LAP degradation product (molecular weight: 38 kDa), and BSA (final concentration: 0.3 mg/ml; molecular weight: 80 kDa) used as an additive. Each separated protein or decomposed product was transferred onto a PVDF membrane by using a semi-dry transferring apparatus. According to the method of Akita et al. (Gastroenterology 123; 352-364, 2002), the membrane was then incubated first with a mouse anti-LAP monoclonal antibody (R & D) at a final concentration of 5 μg/ml or a mouse anti-L59 cleavage section-recognizing monoclonal antibody (homemade; International Publication WO2005/023870) at a final concentration of 20 μg/ml, at room temperature for 60 minutes, and then with a horseradish peroxidase-conjugated goat anti-mouse second antibody (Jackson ImmunoResearch Laboratories) at a final concentration of 1 μg/ml at room temperature for 60 minutes. Bands were then developed using an ECL plus reagent (GE Healthcare), so as to carry out the semi-quantitative analysis of the influence of each peptide on the attenuation of LAP band and the generation of LAP degradation product (FIG. 6).

QP peptide significantly inhibited the LAP cleavage reaction (attenuation of LAP band found in panel A, and generation of LAP degradation product found in panel B) (Lane 3). QPQ peptide inhibited the LAP cleavage reaction more strongly than the QP peptide (Lane 6). In contrast, QPA and T200 peptides exhibited only a weak inhibitory effect (Lanes 4 and 5).

Example 4

In accordance with the method described in Example 1, the influence of each of the QP peptide, QPA peptide, QPQ peptide and T200 peptide on transformation of the cultured hepatic stellate cells, which occurs by culturing cells on a plastic dish, was observed.

Each peptide was dissolved in a medium to a final concentration of 0.5 mM (approximately 500 μg/ml). At the $1^{st}$ day of isolation, the aforementioned cells were treated in a DMEM medium containing 10% FCS. On the $2^{nd}$ day, the medium was changed with serum free DMEM containing 0.1% BSA and each peptide at a final concentration of 0.5 mM, and the culture was further continued for 2 to 7 days. Thereafter, the culture medium was collected as a conditioned medium, and the amount of active TGF-β1 present in the conditioned medium was then quantitated using an ELISA kit manufactured by PROMEGA. At the same time, the state of the cells was observed under a microscope (DMIRB; manufactured by Leica) and photographed.

Figure 7:
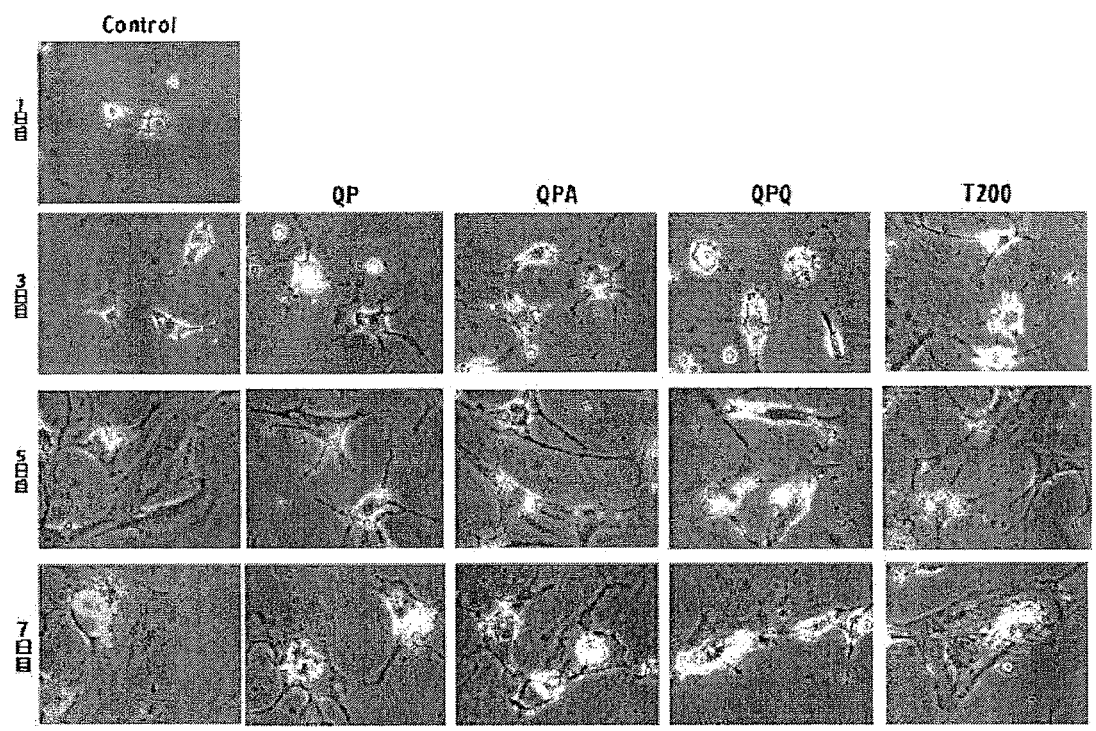
FIG. 7 shows the results of observation seeing influence of the QP, QPA, QPQ, and T200 peptides on transformation of cultured hepatic stellate cells.
Figure 8:
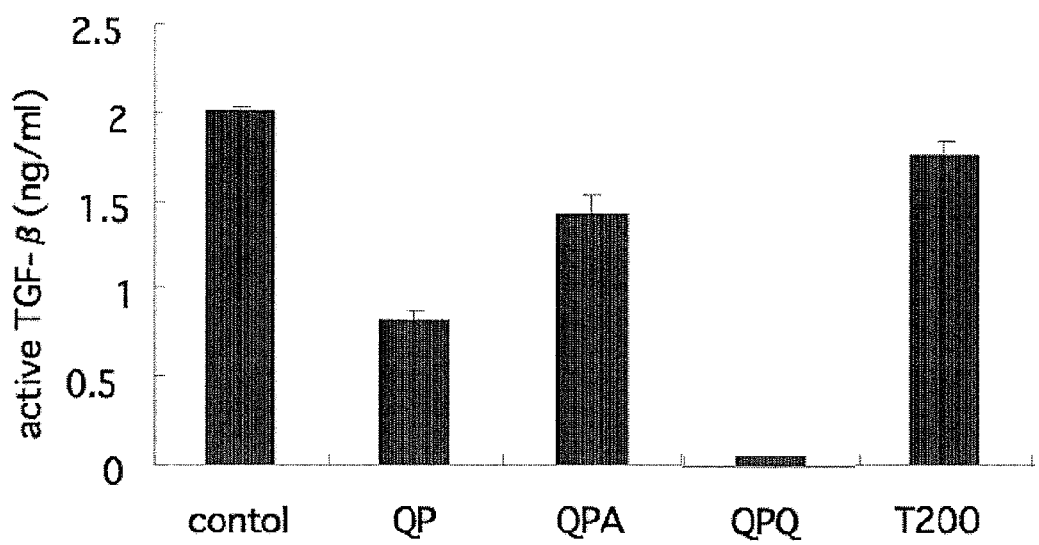
FIG. 8 shows the results of measuring levels of active TGF-β produced in the conditioned medium.

FIG. 7 summarizes the results of the observation under a microscope. All the QP, QPA and QPQ peptides significantly suppressed activation of hepatic stellate cells (a morphological change attended with the disappearance of oil droplets containing vitamin A). In particular, the QPQ peptide exhibited the strongest suppressing effect. In contrast, the 1200 peptide did not exhibit such a suppressing effect.

Table 8 shows the results of measuring the amount of activated TGF-β generated into the conditioned medium. The QP peptide inhibited 55% of generation of the active TGF-β in the conditioned medium observed in control cells, the QPA peptide inhibited 25% thereof, and the QPQ peptide inhibited 90% thereof.

The aforementioned results indicate that the QPQ peptide inhibited the plasmin/plasma kallikrein-dependent TGF-β activation reaction and suppressed the activation of hepatic stellate cells more strongly than the QPA peptide.

Example 5

Improvement of Impaired Liver Regeneration by QP, QPA and QPQ Peptides

Next, in accordance with the method described in Example 2, in vivo effects of the QP, QPA, QPQ, and T200 peptides were examined in LPS-preadministered partially-hepatectomized mice model for impaired liver regeneration (Akita K. et al., Gastroenterology 2002, 123: 352-364).

For the test, 26 five-week-old male C3H/HeN mice were used. After completion of quarantine and environmental acclimatization, the mice were divided into the following 6 groups as shown in Table 4 based on the body weights of the mice on the day of grouping. These include a group to which saline was preadministered and saline was then administered (G1: n=8); a group to which LPS was preadministered and saline was then administered (G2: n=8); a group to which LPS was preadministered and QP peptide was then administered (G3: n=8); a group to which LPS was preadministered and QPA peptide was then administered (G4: n=8); a group to which LPS was preadministered and QPQ peptide was then administered (G5: n=8); and a group to which LPS was preadministered and T200 peptide was then administered (G6: n=8).

TABLE 4

| Group name | Number of mice | Inducer (i.p.) | Sample administered (i.v.) | Systemic perfusion | Mouse No. |
|---|---|---|---|---|---|
| G1 | 8 | Saline | Saline 100 μL/head | Yes | M001 to M004 |
| | | | | No | M005 to M008 |
| G2 | 8 | LPS 7 μg/head | Saline 100 μL/head | Yes | M009 to M012 |
| | | | | No | M013 to M016 |
| G3 | 8 | LPS 7 μg/head | QP peptide | Yes | M017 to M020 |
| | | | 200 μg/100 μL/head/time | No | M021 to M024 |
| G4 | 8 | LPS 7 μg/head | QPA peptide | Yes | M025 to M028 |
| | | | 200 μg/100 μL/head/time | No | M029 to M032 |
| G5 | 8 | LPS 7 μg/head | QPQ peptide | Yes | M033 to M036 |
| | | | 200 μg/100 μL/head/time | No | M037 to M040 |
| G6 | 8 | LPS 7 μg/head | T200 peptide | Yes | M041 to M044 |
| | | | 200 μg/100 μL/head/time | No | M045 to M048 |

After starting the test, 7 μg of LPS (saline in the case of G1) was intraperitoneally administered. Forty-eight hours later, partial hepatectomy was carried out on all the mice. Another forty-eight hours later, all the surviving mice were subjected to an autopsy. In the autopsy, blood was collected. Thereafter, 4 mice from each group were subjected to systemic perfusion with 4% PFA, and the liver was then excised. All the excised lobes were embedded in an embedding agent "Tissue Mount" in a frozen state. On the other hand, the remaining 4 mice from each group were not subjected to systemic perfusion, and a portion of the liver was fixed with formalin, and the remaining portion was collected to be used as a frozen sample (used for mRNA and for protein quantitation). The organ that had been fixed with formalin was processed into a block, and it was then preserved together with the frozen sample in a deep freezer at −80° C.

Test substance

QPQ peptide

Name: TGF-β1 peptide

Amino acid sequence: N-52QILSQQQQASP62-C (SEQ ID NO: 50)

Preservation method: cold storage

LPS Administration Method

Dose: 7 μg/head

Administration route: intraperitoneal administration

Administration volume: 0.1 mL/head

Administration number: once (single administration)

Administration timing: 48 hours before partial hepatectomy

Target animal: G2 to G6 (To G1, saline was administered.)

Administration of Test Substance

Preparation of Peptide-Administered Analyte

Preparation frequency: once

Preparation method: A peptide was dissolved in saline to a concentration of 2 mg/ml, and the resultant was used as a sample to be administered.

Preservation method: The sample was preserved in a refrigerator before use. (The temperature was set at 4° C.)

Peptide Administration Method

Dose: 200 μg/head

Administration route: intravenous administration

Administration volume: 0.1 mL/head

Administration timing: 50, 38, 24, 14 and 2 hours before, and 10, 24 and 34 after partial hepatectomy Number of administration: twice/day, for 4 days (in principle, at 9:00 and at 19:00), 8 times in total Target animal: G2 to G6 (To G1 and G2, saline was administered.)

Partial hepatectomy (⅔ partial hepatectomy; PH)

Treating Method

Each mouse was subjected to inhalation anesthesia with diethyl ether, and the hair ranging from the thorax to the abdomen was shaved. The mouse was immobilized on an autopsy table on its back, and the skin at a surgical site was disinfected with Isodine. The abdomen was excised. Through the excised portion, the hepatic external left lobe, internal right lobe, and internal left lobe were removed from the body, and their roots were bound with a thread. The thus removed liver was cut off. The blood was wiped away, and the opened abdomen was then closed with a staple. The treatment was terminated by disinfecting the skin with Isodine.

Number of mice treated: all the 48 mice

Treating timing: 48 hours after administration of LPS

Autopsy

Autopsy timing: 48 hours after partial hepatectomy (PH)

Autopsy Method

Pentobarbital sodium at a dose of 40 mg/kg was intraperitoneally administered to the mice, so that they were then anesthetized. Thereafter, using an untreated syringe, as large amount as possible of blood was collected from the abdominal aorta, so as to cause death to the mice due to exsanguination.

After completion of the blood collection, 4 mice from each group were subjected to systemic perfusion with 4% PFA, and the liver was then excised from each mouse. All the excised lobes were embedded in an embedding agent "Tissue Mount" in a frozen state. On the other hand, the remaining 4 mice from each group were not subjected to systemic perfusion, and a portion of the liver was fixed by immersing it in a 10% formalin solution, and the remaining portion was frozen with liquid nitrogen and it was preserved in the form of a frozen sample (used for mRNA and for protein quantitation).

Measurement of Hepatic Contents of TGF-β1

A liver extract was prepared from approximately 30 mg of the hepatic tissues prepared for the use in protein quantitation in 11.2 above, according to the method of Okuno M. et al. (Okuno M. et al., Gastroenterology 2001; 120: 1784-1800). The amount of TGF-β1 in the extract was determined using an ELISA kit manufactured by PROMEGA. The amount of TGF-β1 was presented as a pg/mg protein of the sample. Other conditions were the same as those described in Example 2.

(Results of Observation of General Condition)

In the LPS-administered groups, a decrease in autonomic movement and piloerection were confirmed by observation conducted 12 hours after the administration of LPS.

(Results of Staining)

Figure 9:
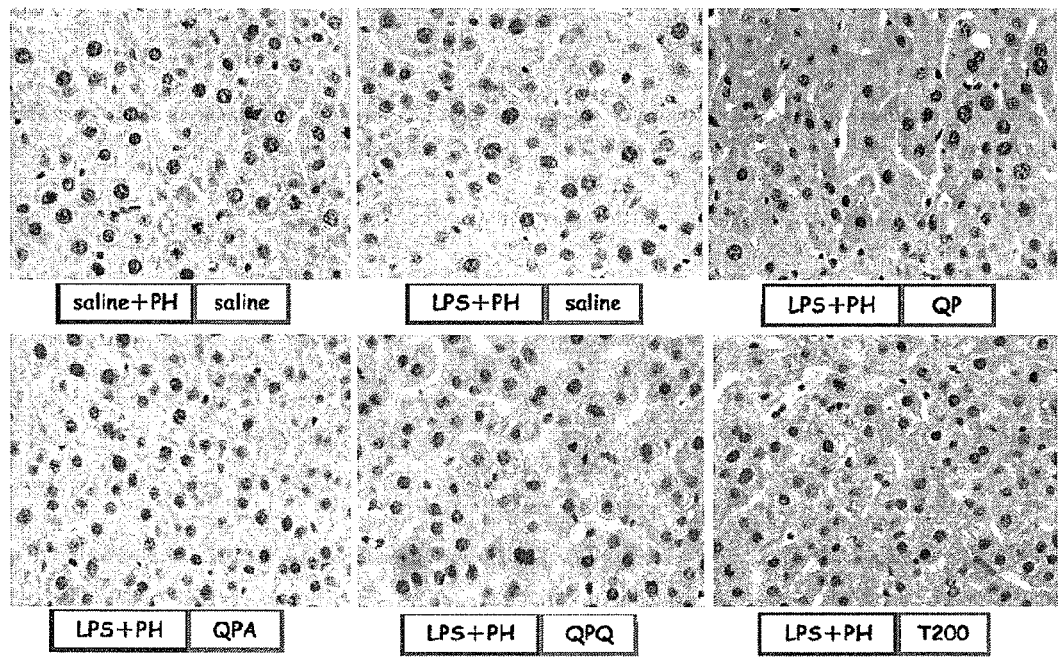
FIG. 9 shows the improvement of impaired liver regeneration by the QP, QPA, and QPQ peptides (photographs).

FIG. 9 shows the results of staining. By administering the QP, QPA or QPQ peptide to the mice, impaired liver regeneration caused by preadministration of LPS was significantly improved (it had been shown that impaired liver regeneration is ascribed to the plasma kallikrein-dependent TGF-β activation reaction; Akita et al., Gastroenterology 123: 352-364, 2002). The levels of such an improving effect are almost similar between the QP, QPA and QPQ peptides. In contrast, the T200 peptide did not exhibit such an improving effect.

(Results of Quantitation)

Figure 10:
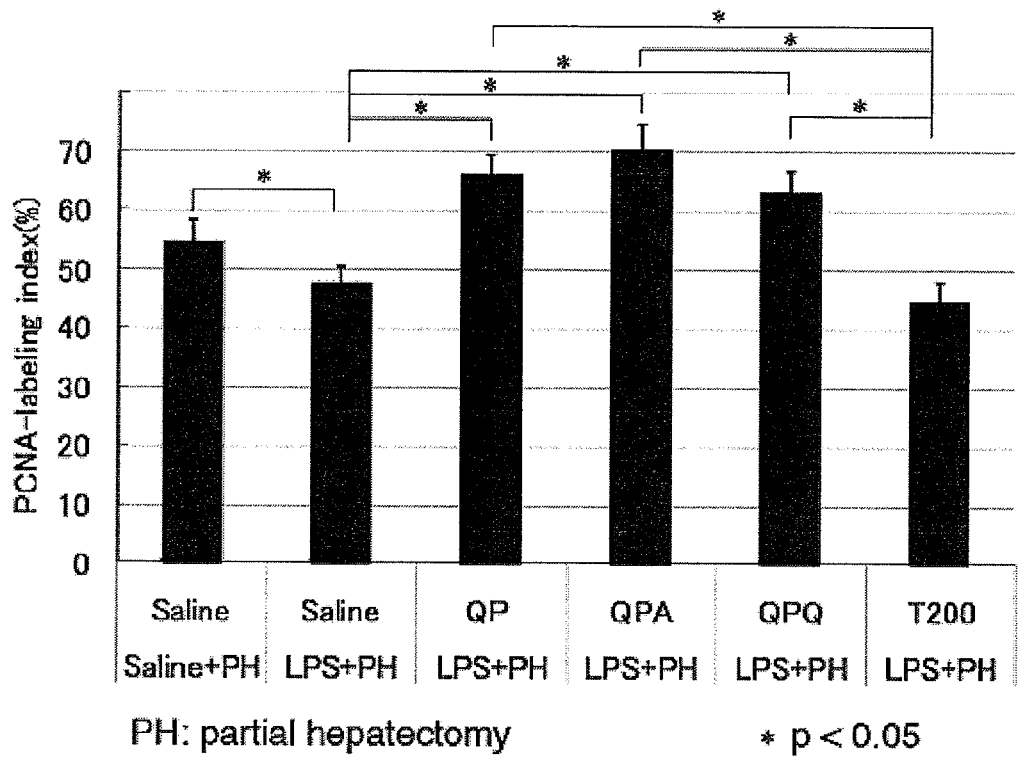
FIG. 10 shows the improvement of impaired liver regeneration by the QP, QPA, and QPQ peptides (quantitation).

The results obtained by quantitating the aforementioned staining results with the percentage of PCNA positive hepatic cells are delineated in FIG. 10. Following administration of the QP, QPA, or QPQ peptide to the mice, the percentage of impaired liver regeneration, induced by preadministration of LPS (the percentage of PCNA positive cells was reduced from 55% to 47%, and it had been demonstrated that this is because of the plasma kallikrein-dependent TGF-β activation reaction; Akita et al., Gastroenterology 123: 352-364, 2002), was improved. The percentage of PCNA positive cells was increased to 66%, 70% and 64%, respectively, following administration of QP peptide, QPA peptide and QPQ peptide, and thus these peptides are thought to exhibit an impaired liver regeneration-improving and/or a liver regeneration-promoting effect. In contrast, the P200 peptide did not exhibited any such improving effects (45%).

(Results of Quantitation of Hepatic Contents of TGF-β1)

Figure 11:
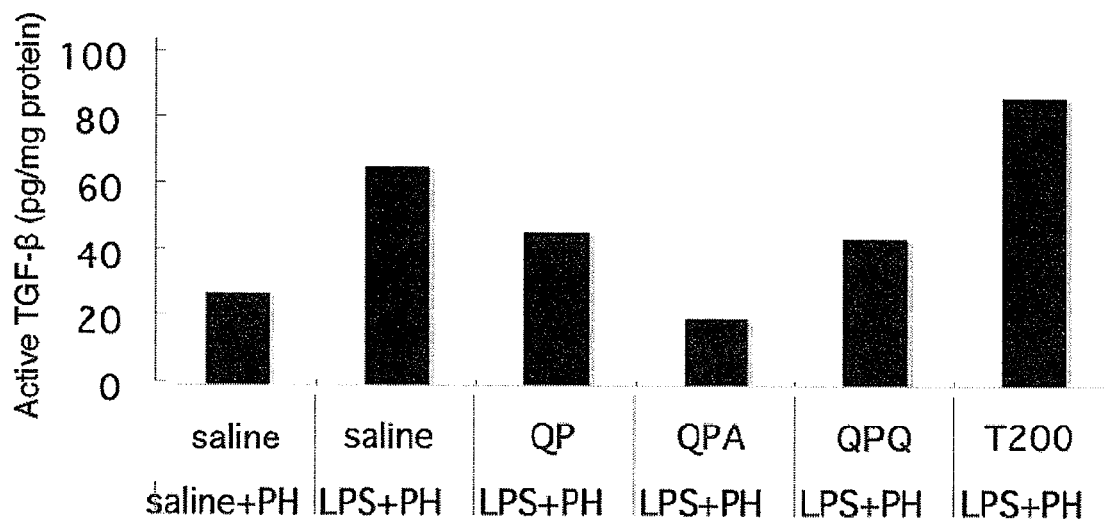
FIG. 11 shows the results of measuring hepatic contents of TGF-β1.

FIG. 11 summarizes the results of measuring the hepatic contents of TGF-β1. By preadministration of LPS, the hepatic contents of TGF-β1 increased approximately 2.3 times higher than the value of the control group. The QP peptide, the QPA peptide and the QPQ peptide prevented such an increase and kept the value to approximately 1.6 times, 0.7 times and 1.6 times higher than the value of the control group, respectively. In contrast, the T200 peptide did not exhibit such a suppressing effect, rather increased the value (3.1 times).

(Summary and Consideration)

As stated above, it was suggested that low concentrations of all the QP peptide, QPA peptide and QPQ peptide, derived from the cleavage sequences of latent TGF-β1 LAP portions by TGF-β-activating proteases, suppress the proteolytic TGF-β activation reaction that causes liver diseases, inhibit the generation of active TGF-β, and improve liver regeneration.

In vitro, the QP peptide is degraded and then disappears. Therefore, although it strongly forms an enzyme-substrate complex, the QP peptide would exhibit a weak inhibitory activity in a cell culture system or in an animal model. In contrast, although the QPA peptide forms such an enzyme-substrate complex with weaker ability than that of the QP peptide, the generated enzyme-substrate complex is resistant to the cleavage and stably exists. Therefore, the QPA peptide is considered to exhibit more potent inhibitory action than the QP peptide in a cell culture system or in an animal model.

The T200 peptide in vitro is considered to exhibit a weak binding ability to proteases through sequence-nonspecific trapping effects. However, because the QPA peptide has higher ability to form an enzyme-substrate complex than the T200 peptide in a cell culture system or in an animal model, the QPA peptide is considered to exhibit a higher inhibitory effect than the T200 peptide.

The QPQ peptide maintains a high ability to form an enzyme-substrate complex not cleavable by proteases. Thus, it is considered that this peptide exhibited the strongest inhibitory activity in all types of evaluation systems including an in vitro system, a cell culture system, and an animal model. Namely, comparing to the QP and QPA peptides, the QPQ peptide can more stably inhibit a TGF-β activation reaction occurring during the pathogenesis of the diseases, and therefore provides the basis for developing a preventive agent and/or a therapeutic method against TGF-β-related diseases including various types of sclerotic diseases as typical examples through applying the present peptide and a derivative thereof.

The invention claimed is:

1. A peptide consisting of 11 to 50 amino acid residues, which comprises an amino acid sequence, Gln-Ile-Leu-Ser-X1-X2-X3-X4-Ala-Ser-Pro (SEQ ID NO: 1) wherein each of X1 to X4 independently represents any amino acid residue, and X1-X2-X3-X4 is a sequence that is not Lys-Leu-Arg-Leu (SEQ ID NO: 12) and is not cleavable by plasmin and/or plasma kallikrein.

2. The peptide according to claim 1, wherein X1 and X3 represent amino acid residues other than basic amino acids.

3. A peptide consisting of 11 to 50 amino acid residues, which comprises the amino acid sequence of any one of the following (1) to (4):

(SEQ ID NO: 2)
Gln-Ile-Leu-Ser-Ala-Ala-Ala-Ala-Ala-Ser-Pro (1);

(SEQ ID NO: 3)
Gln-Ile-Leu-Ser-Ala-Leu-Ala-Leu-Ala-Ser-Pro (2);

(SEQ ID NO: 4)
Gln-Ile-Leu-Ser-Gln-Gln-Gln-Gln-Ala-Ser-Pro (3);
and (SEQ ID NO: 5)
Gln-Ile-Leu-Ser-Gln-Leu-Gln-Leu-Ala-Ser-Pro (4).

4. The peptide according to claim 1, which has a length of 11 to 20 amino acid residues.

5. An inhibitor composition comprising the peptide of claim 1 and a carrier, wherein the peptide inhibits the generation of active TGF-β.

6. A medicament comprising the peptide of claim 1 and a carrier.

7. A hepatic regeneration promoting composition or hepatic fibrosis suppressing composition, which comprises the peptide of claim 1 and a carrier.

* * * * *

SEQUENCE LISTING

```
<160> NUMBER OF SEQ ID NOS: 50

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(8)
<223> OTHER INFORMATION: Any amino acid
<220> FEATURE:
<223> OTHER INFORMATION: see specification as filed for detailed
      description of substitutions and preferred embodiments

<400> SEQUENCE: 1

Gln Ile Leu Ser Xaa Xaa Xaa Xaa Ala Ser Pro
```

-continued

```
<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gln Ile Leu Ser Ala Ala Ala Ala Ala Ser Pro
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ile Leu Ser Ala Leu Ala Leu Ala Ser Pro
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ile Leu Ser Gln Gln Gln Gln Ala Ser Pro
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Ile Leu Ser Gln Leu Gln Leu Ala Ser Pro
1               5                   10

<210> SEQ ID NO 6
<211> LENGTH: 51
<212> TYPE: PRT
<213> ORGANISM: Homo sapiens

<400> SEQUENCE: 6

Thr Cys Lys Thr Ile Asp Met Glu Leu Val Lys Arg Lys Arg Ile Glu
1               5                   10                  15

Ala Ile Arg Gly Gln Ile Leu Ser Lys Leu Arg Leu Ala Ser Pro Pro
            20                  25                  30

Ser Gln Gly Glu Val Pro Pro Gly Pro Leu Pro Glu Ala Val Leu Ala
        35                  40                  45

Leu Tyr Asn
    50
```

```
<210> SEQ ID NO 7
<211> LENGTH: 51
<212> TYPE: PRT
<213> ORGANISM: Homo sapiens

<400> SEQUENCE: 7

Thr Cys Ser Thr Leu Asp Met Asp Gln Phe Met Arg Lys Arg Ile Glu
 1               5                  10                  15

Ala Ile Arg Gly Gln Ile Leu Ser Lys Leu Lys Leu Thr Ser Pro Pro
             20                  25                  30

Glu Asp Tyr Pro Glu Pro Glu Glu Val Pro Pro Glu Val Ile Ser Ile
         35                  40                  45

Tyr Asn Ser
     50

<210> SEQ ID NO 8
<211> LENGTH: 51
<212> TYPE: PRT
<213> ORGANISM: Homo sapiens

<400> SEQUENCE: 8

Thr Cys Thr Thr Leu Asp Phe Gly His Ile Lys Lys Lys Arg Val Glu
 1               5                  10                  15

Ala Ile Arg Gly Gln Ile Leu Ser Lys Leu Arg Leu Thr Ser Pro Pro
             20                  25                  30

Glu Pro Thr Val Met Thr His Val Pro Tyr Gln Val Leu Ala Leu Tyr
         35                  40                  45

Asn Ser Thr
     50

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Ile Leu Ser Lys Leu Arg Leu Ala Ser Pro
 1               5                  10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ile Leu Ser Ala Ala Ala Leu Ala Ser Pro
 1               5                  10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Gly Val Val Arg Gln Trp Leu Ser Arg Gly
```

```
                1               5                    10
```

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Leu Arg Leu
1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Ile Arg Gly
1

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu Ala Ile Arg Gly
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ile Glu Ala Ile Arg Gly
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ile Glu Ala Ile Arg Gly
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Lys Arg Ile Glu Ala Ile Arg Gly
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Lys Arg Ile Glu Ala Ile Arg Gly
1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Arg Lys Arg Ile Glu Ala Ile Arg Gly
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Lys Arg Lys Arg Ile Glu Ala Ile Arg Gly
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Val Lys Arg Lys Arg Ile Glu Ala Ile Arg Gly
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Glu Leu Val Lys Arg Lys Arg Ile Glu Ala Ile Arg Gly
1               5                   10

<210> SEQ ID NO 23

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Met Glu Leu Val Lys Arg Lys Arg Ile Glu Ala Ile Arg Gly
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Met Glu Leu Val Lys Arg Lys Arg Ile Glu Ala Ile Arg Gly
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ile Asp Met Glu Leu Val Lys Arg Lys Arg Ile Glu Ala Ile Arg Gly
1               5                   10                  15

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Ile Asp Met Glu Leu Val Lys Arg Lys Arg Ile Glu Ala Ile Arg
1               5                   10                  15

Gly

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Thr Ile Asp Met Glu Leu Val Lys Arg Lys Arg Ile Glu Ala Ile
1               5                   10                  15

Arg Gly

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic
```

-continued

```
      peptide

<400> SEQUENCE: 28

Cys Lys Thr Ile Asp Met Glu Leu Val Lys Arg Lys Arg Ile Glu Ala
1               5                   10                  15

Ile Arg Gly

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Cys Lys Thr Ile Asp Met Glu Leu Val Lys Arg Lys Arg Ile Glu
1               5                   10                  15

Ala Ile Arg Gly
            20

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Pro Ser Gln Gly
1

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Pro Ser Gln Gly Glu
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Pro Ser Gln Gly Glu Val
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33
```

```
Pro Ser Gln Gly Glu Val Pro
1               5
```

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

```
Pro Ser Gln Gly Glu Val Pro Pro
1               5
```

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
Pro Ser Gln Gly Glu Val Pro Pro Gly
1               5
```

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Pro Ser Gln Gly Glu Val Pro Pro Gly Pro
1               5                   10
```

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Pro Ser Gln Gly Glu Val Pro Pro Gly Pro Leu
1               5                   10
```

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Pro Ser Gln Gly Glu Val Pro Pro Gly Pro Leu Pro
1               5                   10
```

<210> SEQ ID NO 39
<211> LENGTH: 13
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 39

Pro Ser Gln Gly Glu Val Pro Pro Gly Pro Leu Pro Glu
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Pro Ser Gln Gly Glu Val Pro Pro Gly Pro Leu Pro Glu Ala
1               5                   10

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Ser Gln Gly Glu Val Pro Pro Gly Pro Leu Pro Glu Ala Val
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Pro Ser Gln Gly Glu Val Pro Pro Gly Pro Leu Pro Glu Ala Val Leu
1               5                   10                  15

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Pro Ser Gln Gly Glu Val Pro Pro Gly Pro Leu Pro Glu Ala Val Leu
1               5                   10                  15

Ala

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Pro Ser Gln Gly Glu Val Pro Pro Gly Pro Leu Pro Glu Ala Val Leu
1               5                   10                  15

Ala Leu

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Pro Ser Gln Gly Glu Val Pro Pro Gly Pro Leu Pro Glu Ala Val Leu
1               5                   10                  15

Ala Leu Tyr

<210> SEQ ID NO 46
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Pro Ser Gln Gly Glu Val Pro Pro Gly Pro Leu Pro Glu Ala Val Leu
1               5                   10                  15

Ala Leu Tyr Asn
            20

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Ile Leu Ser Lys Leu Arg Leu Ala Ser Pro
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Ile Leu Ser Ala Ala Ala Ala Ala Ser Pro
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Gly Val Val Arg Gln Trp Leu Ser Arg Gly
1               5                   10

```
<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Ile Leu Ser Gln Gln Gln Gln Ala Ser Pro
1               5                   10
```